US007875752B2

(12) United States Patent
Gladysz et al.

(10) Patent No.: US 7,875,752 B2
(45) Date of Patent: Jan. 25, 2011

(54) RECOVERY METHOD FOR CATALYSTS, REAGENTS AND CO-PRODUCTS

(75) Inventors: John Andrew Gladysz, Erlangen (DE); Marc Oliver Wende, Dachau (DE); Dennis P. Curran, Pittsburgh, PA (US)

(73) Assignee: Fluorous Technologies Incorporated, Pittsburgh, PA (US)

( * ) Notice: Subject to any disclaimer, the term of this patent is extended or adjusted under 35 U.S.C. 154(b) by 0 days.

(21) Appl. No.: 10/664,105

(22) Filed: Sep. 17, 2003

(65) Prior Publication Data

US 2004/0127755 A1 Jul. 1, 2004

Related U.S. Application Data

(60) Provisional application No. 60/411,439, filed on Sep. 17, 2002.

(51) Int. Cl.
*C07C 17/38* (2006.01)
*C01B 9/08* (2006.01)
*C01D 3/02* (2006.01)

(52) U.S. Cl. .................. 570/179; 423/489; 423/490

(58) Field of Classification Search ............. 556/454, 556/450, 476, 485; 560/232, 234, 179, 183; 568/309
See application file for complete search history.

(56) References Cited

U.S. PATENT DOCUMENTS

| 5,777,121 | A | 7/1998 | Curran et al. | |
|---|---|---|---|---|
| 5,859,247 | A | 1/1999 | Curran et al. | |
| 6,156,896 | A | 12/2000 | Curran et al. | |
| 6,673,539 | B1 | 1/2004 | Wipf et al. | |
| 6,734,318 | B2 * | 5/2004 | Curran et al. | 556/454 |
| 6,749,756 | B1 | 6/2004 | Curran et al. | |
| 6,815,390 | B2 * | 11/2004 | Vaughan et al. | 502/150 |
| 6,861,544 | B1 * | 3/2005 | Curran et al. | 556/88 |
| 2003/0125590 | A1 | 7/2003 | Curran et al. | |
| 2003/0148878 | A1 * | 8/2003 | Vaughan et al. | 502/159 |
| 2005/0015936 | A1 * | 1/2005 | Eckert et al. | 23/295 R |

FOREIGN PATENT DOCUMENTS

WO   WO 02/04120 A2   1/2002
WO   WO 02/096550 A1   12/2002

OTHER PUBLICATIONS

Wende et al., Journal of the American Chemical Society, 2001, 123, 11490-11491.*
Crystallization in Kirk-Othmer Encyclopedia of Chemical Technology Copyright © 2001 by John Wiley & Sons, Inc.*
Wende et al., J. Am. Chem. Soc. 2001, 123, 11490-11491.*
Curran et al., Synlett 2001, No. 9, 1488-1496.*
U.S. Appl. No. 09/565,087, filed May 5, 2000, Curran et al.
U.S. Appl. No. 09/932,903, filed Aug. 20, 2001, Curran et al.
I.T. Horvath, J. Rabal; "Facile catalyst separation without water: Flourous biphase hydroformylation of olefins", *Science* 1994, 266, 72-75.
N.D. Danielson, L.G. Beaver, J. Wangsa; "Fluoropolymers and fluorocarbon bonded phases as column packings for liquid chromatography", *Journal of Chromatography* 1991, 544, 187-199.
D.P. Curran; "Fluorous Techniques for Synthesis of Organic Molecules: A Unified Strategy for Reaction and Separation", *Stimulating Concepts in Chemistry*; F. Vögtle, J.F. Stoddardt and M. Shibasaki, Ed.; Wiley-VCH: New York, 2000; pp. 25.
D.P. Curran; "Fluorous reverse phase silica gel. A new tool for preparative separations in synthetic organic and organofluorine chemistry", *Synlett* 2001, 1488-1496.
K. Ishihara, S. Kondo, H.Yamamoto; "3,5-Bis (Perfluorodecyl) phenylboronic acid as an easily recyclable direct amide condensation catalyst", *Synlett* 2001, 1371-1374.
D.E. Bergbreiter, J.G. Franchina; "A Soluble Fluorous Phase Polymer Support", *Chemical Commununications*, 1997, 1531-1532.
D.E. Bergbreiter, P.L. Osburn, A. Wilson, E.M. Sink; "Palladium-Catalyzed C-C Coupling under Thermomorphic Conditions", *Journal of the American Chemical Society*, 2000, 122, 9058-9064.
K. Olofsson, S.Y. Kim, M. Larhed, D.P. Curran, A. Hallberg; "High-speed, highly fluorous organic reactions", *Journal of Organic Chemistry*, 1999, 64, 4539-4541.
K. Mikami, Y. Mikami, Y. Matsumoto, J. Nishikido, F. Yamamoto, H. Nakajima; "Lewis acid catalysis by lanthanide complexes with tris(Perfluorooctanesulfonyl)methide ponytails in fluorous recyclable phase", *Tetrahedron Letters*, 2001 42, 289-292.
J.N. Xiang, A. Orita, J. Otera; "Fluoroalkyldistannoxane catalysts for transesterification in fluorous biphase technology", *Advanced Synthesis & Catalysis*, 2002, 344, 84-90.
Errede, L.A., et al. "Reactive Microporous Composite Membranes," in *Chemically Modified Surfaces*, vol. 2, *Chemically Modified Surfaces in Science and Industry*, Leyden, D.E., and Collins W.T. eds., Gordon and Breach Science Publishers, New York, 1988, pp. 91-104.

* cited by examiner

*Primary Examiner*—Karl J Puttlitz
(74) *Attorney, Agent, or Firm*—K&L Gates LLP

(57) ABSTRACT

The present invention provides a method for conducting a chemical reaction in a non-fluorous medium using a fluorous compound in the presence of a solid adsorbant containing a fluorous domain and at least one chemical reactant, comprising contacting the fluorous compound and at least one chemical reactant under conditions that form at least one product.

68 Claims, No Drawings

RECOVERY METHOD FOR CATALYSTS,
REAGENTS AND CO-PRODUCTS

CROSS REFERENCE TO RELATED APPLICATIONS

This application claims priority to U.S. Provisional Patent Application, Ser. No. 60/411,439, entitled "Recovery Method for Catalyst, Reagents and Co-Products", filed Sep. 17, 2002, which is incorporated by reference herein in its entirety.

FIELD OF THE INVENTION

The present invention relates to novel recovery and separation methods of reactive fluorous catalysts, reagents and co-products during and after chemical transformations.

BACKGROUND OF THE INVENTION

It is generally the case that organic compounds must be synthesized as pure substances through well-planned reactions and scrupulous separation/purification. In fields such as drug discovery, catalyst design and new material development, tens of thousands of organic compounds must be synthesized and tested to discover a few active ones. In the pharmaceutical industry, for example, synthesizing large numbers of compounds in the traditional way is ineffective relative to the rapid emergence of new biological targets. A major factor limiting the productivity of orthodox solution (liquid) phase organic synthesis is the time consuming process of purification. High throughput organic synthesis, therefore, preferably integrates organic reactions with rapid purification/separation procedures.

Recently, fluorous synthetic and separation techniques have attracted the interest of organic chemists. In fluorous synthetic techniques, reaction components are typically attached to fluorous groups or tags such as perfluoroalkyl groups to facilitate the separation of products. Organic compounds are readily rendered fluorous by attachment of an appropriately fluorinated phase label or tag. In general, fluorous-tagged molecules partition preferentially into a fluorous phase. This fluorous phase is typically insoluble in organic or inorganic solvents under standard reaction conditions. This characteristic of fluorous compounds has lead to the development of fluorous biphasic catalysis (I. T. Horvath and J. Rabai, *Science,* 1994, 266, 72). Fluorous biphasic catalysis provides a simple solution to the product/reagent or product/catalyst separation problems inherent in chemical systems. By utilizing a fluorous reagent or catalyst, separation of the fluorous reaction components from the organic reaction components is accomplished via a fluorous phase/organic phase liquid/liquid or liquid/solid separation protocol wherein the fluorous reagent or catalyst selectively partitions into the fluorous phase and the organic products partition into the organic phase. Fluorous separation techniques include, but are not limited to, fluorous liquid-liquid extraction, fluorous solid phase extraction, and fluorous chromatography. See, for example, Danielson, N. D. et al., "*Fluoropolymers and Fluorocarbon Bonded Phases as Column Packings for Liquid Chromatography,*" *J. Chromat.,* 1991, 544, 187-199; Curran, D. P. "*Fluorous Reverse Phase Silica Gel. A New Tool for Preparative Separations in Synthetic Organic and Organofluorine Chemistry,*" *Synlett,* 2001, 9, 1488; Curran D. P., "Fluorous Techniques for the Synthesis of Organic Molecules: A Unified Strategy for Reaction and Separation." In: *Stimulating Concepts in Chemistry* (M. Shibasaki, J. Fraser Stoddart and F. Vögtle, eds.), Wiley-VCH, Weinheim, 2000, 25. Several fluorous reaction and separation techniques are disclosed, for example, in U.S. Pat. Nos. 6,156,896; 5,859,247 and 5,777,121, the disclosures of which are incorporated herein by reference in their entirety. In addition, several fluorous reaction and separation techniques are disclosed in U.S. patent application Ser. Nos. 09/506,779; 09/565,087; 09/583,247; 09/932,903; 09/977,944 and 10/094,345, the disclosures of which are incorporated by reference herein in their entirety.

However, the use of fluorous and perfluorous liquids as reaction or separation solvents may have potential drawbacks. It is well known that low molecular weight fluorocarbons (freons) are greenhouse gases whose release into the atmosphere has environmental consequences. While most fluorous solvents are typically higher molecular weight fluorocarbons, they typically have long environmental half-lives and their environmental impact is less well known. In addition, fluorinated solvents are typically more expensive than their organic counterparts. Therefore, it would be desirable to have a system with the separation advantages of fluorous components without the use of fluorous reaction and/or separation solvents.

Recent reports demonstrate some advances that limit the use of fluorous solvents while still retaining the advantages of fluorous separation techniques. Yamamoto, et al. have reported a fluorous catalyst system that uses liquid/solid extraction to remove the fluorous catalyst from the reaction mixture by precipitation of the catalyst at low temperature (K. I. Ishihara, S. Kondo, H. Yamamoto, *Synlett,* 2001, 9, 1371). This method has limited application because it requires the use of fluorous catalysts having specific inherent solubility characteristics such that the catalyst will precipitate in solid form for removal. Eckert, et al. have disclosed a method which eliminates the use of fluorous solvents, utilizing the increased solubility of fluorous compounds in organic solvents saturated with dissolved gaseous $CO_2$ (C. A. Eckert, P. G. Jessop, C. L. Liotta, International Patent Application No. PCT/US02/17110). This method requires the use of gaseous $CO_2$ under pressures in the range of 30-300 bar, and reaction equipment capable of withstanding pressurization. Accordingly, this method requires the use of specialized equipment that is relatively costly and more hazardous than other known fluorous reaction/separation techniques. Vaughan, et al. have disclosed a fluorous biphasic catalyst wherein the catalyst is supported on functionalized polymeric beads (J. F. S. Vaughan, M. G. Pellatt, J. Sherrington, E. G. Hope, U.S. patent application Ser. No. U.S. 2003/0148878 A1, and International Patent Application No. PCT/EP01/06676). However, this method still requires the use of fluorous reaction solvents to facilitate the reaction, albeit in reduced volumes.

By combining reaction and separation features, the present invention also has advantages over standard fluorous solid phase extractions (spe), which pertain only to the separation part of a chemical synthesis. In fluorous spe's, a crude product after completion of a chemical reaction is typically added to fluorous silica gel and eluted with a suitable fluorophobic solvent followed by a fluorophilic solvent. Sometimes, the silica gel is added to the reaction mixture after the reaction is complete, and then the slurry is loaded directly (or evaporated and then loaded) onto a fluorous silica column to complete the spe with the usual fluorophobic and fluorophilic solvent extractions. Compared to the simple solid-liquid separation techniques used in the present invention, spe uses much more solvent and fluorous silica gel, is more time consuming and expensive, and does not allow for the conveniences and advantages of having supports present during the reaction.

It would therefore be desirable to develop methods that incorporate the benefits of fluorous biphasic reaction/catalysis processes, i.e. ready separation of fluorous reagents and/or catalysts from non-fluorous reaction components, while not requiring the use of fluorous solvents, pressurized reaction environments and/or specific precipitation characteristics of the fluorous reaction component.

SUMMARY OF THE INVENTION

The present invention describes a new recovery method for fluorous catalysts, reagents, transformed reagents (co-products) or other reaction components such as, substrates, reactants, scavengers, side-products or target products, subsequent to any process or chemical reaction that uses such a catalyst or reagent. The present invention provides a significant advance over prior art in that a fluorous solvent is no longer needed to recover the fluorous catalyst, reagent, or transformed reagent.

The present invention allows the recovery of the fluorous catalyst, reagent, or transformed reagent by a liquid/solid phase separation, wherein the solid is the desired fluorous catalyst, reagent, or transformed reagent that has been absorbed onto a solid phase or any support that affords the solid at the low temperature limit. The adsorbant can be present before the reaction (i.e. the reagent or catalyst is supported) and/or during the reaction, or it may be added during the reaction or after the reaction is complete. After recovery by liquid/solid phase separation, an absorbed fluorous catalyst can be directly used in a subsequent reaction. The fluorous catalyst or reagent has less affinity for the adsorbant at the high temperature limit, needed for reaction, and is therefore available and free to react in solution.

In one embodiment, the present invention provides a method for conducting a chemical reaction in a non-fluorous medium using a fluorous compound in the presence of a solid adsorbant containing a fluorous domain and at least one chemical reactant, comprising contacting the fluorous compound and at least one chemical reactant under conditions that form at least one product.

In another embodiment, the present invention provides a method for conducting a chemical reaction in a non-fluorous medium using a fluorous compound in the presence of a solid adsorbant containing a fluorous domain and at least one chemical reactant, wherein the fluorous compound is initially absorbed on the solid adsorbant containing the fluorous domain, comprising contacting the fluorous compound and at the least one chemical reactant under conditions that form at least one product.

In yet another embodiment, the present invention provides a method for conducting a chemical reaction in a non-fluorous medium using a fluorous compound and at least one chemical reactant. The method includes contacting the fluorous compound and at least one chemical reactant under conditions that form at least one product, adding a fluorous domain-containing solid adsorbant, and reducing the temperature of the chemical reaction from a first temperature to a second temperature such that the solubility of the fluorous compound in the non-fluorous medium decreases and the amount of the fluorous compound absorbed on the solid adsorbant containing a fluorous domain increases.

In a further embodiment, the present invention provides for a method for conducting a chemical reaction using a fluorous compound in a non-fluorous medium, in the presence of a solid adsorbant containing a fluorous domain and at least one chemical reactant, wherein the fluorous compound is initially absorbed on the solid adsorbant containing the fluorous domain, comprising increasing the temperature of the chemical reaction from a first temperature to a second temperature, such that the solubility of the fluorous compound in the non-fluorous medium increases and the amount of the fluorous compound absorbed on the solid adsorbant containing a fluorous domain decreases; contacting the fluorous compound and at least one chemical reactant under conditions that form at least one product; and reducing the temperature from the second temperature to a third temperature, such that the solubility of the fluorous compound in the non-fluorous medium decreases and the amount of the fluorous compound absorbed on the solid adsorbant containing a fluorous domain increases.

It should be understood that this invention is not limited to the embodiments disclosed in this summary, and it is intended to cover modifications that are within the spirit and scope of the inventions, as defined by the claims.

DETAILED DESCRIPTION OF THE EMBODIMENTS OF THE INVENTION

Other than in the operating examples, or where otherwise indicated, all numbers expressing quantities of ingredients, reaction conditions and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The present invention describes a new recovery method for fluorous catalysts, reagents, transformed reagents (co-products) or other reaction components such as, for example, substrates, reactants, scavengers, side-products or target products, subsequent to any process or chemical reaction that uses such a catalyst or reagent. The present invention provides a significant advance over prior art in that a fluorous solvent is no longer needed to recover the fluorous catalyst, reagent, or transformed reagent.

The temperature dependent solubilities of fluorous catalysts, reagents, and transformed reagents are now well established. The present invention pertains to fluorous catalysts or reagents that are partially soluble or insoluble at a "low temperature limit" in a non-fluorous medium. As used herein, the term "non-fluorous medium" refers, generally, to an organic or inorganic ($H_2O$, $CS_2$, etc) liquid medium, or any mixture thereof, or any liquid medium comprised solely of reactants and/or products ("solvent-free reaction"), or any supercritical fluids. The term "non-fluorous medium" is understood as not including gaseous solutes beyond those trace amounts of gas typically dissolved in the medium. As used herein, the term "high temperature limit" refers, generally, to the reaction temperature for the process of interest, and the term "low temperature limit" refers, generally, to a temperature lower than the reaction temperature for the process of interest, for example, but not limited to, room temperature, 0° C., dry ice temperature and intermediate temperatures. As used herein, "partially soluble" may be defined as less than 0.01 M (moles per liter). As used herein, the term "solid" refers, generally, to a non-free flowing substance, for example, but not limited to, precipitates, residues, crystals, powders, gels, gums, tars, greases, viscous liquids and similar substances.

The present invention allows the recovery of the fluorous catalyst, reagent, or transformed reagent by a liquid/solid phase separation, where the solid is the desired fluorous catalyst, reagent, or transformed reagent that has been absorbed onto a solid phase or any support that affords a solid at the low temperature limit. The adsorbant can be present before the reaction (i.e. the reagent or catalyst is supported) and/or during the reaction, or it may be added during the reaction or after the reaction is complete. After recovery by liquid/solid phase separation, an absorbed fluorous catalyst can be directly used in a subsequent reaction. The fluorous catalyst or reagent has less affinity for the adsorbant at the high temperature limit, needed for reaction, and is therefore available and free to react in solution. As used herein, the term "absorbed" refers, generally, to substantially any association between the fluorous domain on the solid adsorbant and the fluorous compound. Examples of adsorbed include, but are not limited to, physically partitioned, chemically partitioned, deposited, oiled-out, precipitated onto or dissolved into the adsorbant.

It has been found that adsorbants that contain fluorous domains are uniquely able to scavenge and absorb fluorous catalysts, reagents, and transformed reagents. Adsorbants without fluorous domains give poorer performance characteristics in comparison to analogous materials with fluorous domains. Examples of adsorbants that are part of this invention include, but are not limited to, the following:

(1) Teflon® shavings (Teflon is a registered trademark of DuPont for polytetrafluoroethylene) and other polytetrafluoroethylene shavings;

(2) high-surface area forms of Teflon® and other forms of polytetrafluoroethylene, for example Teflon® that has been deliberately damaged, etched, or modified by chemical or mechanical means;

(3) non-commercial grades or analogs of Teflon®, which may be in-situ generated, of lower molecular weight, contain structural defects, impurities, or co-monomers that may disrupt the regular structure;

(4) all other perfluorinated or highly fluorinated polymers;

(5) non-fluorous polymers (polyamides, polyolefins, polyesters, etc.) or biomaterials into which fluorous domains have been incorporated, for example by copolymerization, functionalization, grafting, or other techniques;

(6) inorganic oxides such as alumina or silica onto which fluorous domains have been introduced, for example by absorption or covalent attachment (for example, fluorous silica gel or FluoroFlash™ silica gel, commercially available from Fluorous Technologies Inc. (Pittsburgh, Pa.));

(7) all other solid polymeric or extended domain materials including binary phases, tertiary phases, single crystals, supramolecular compounds, etc. onto which fluorous domains have been introduced, for example by absorption or covalent attachment; and (8) analogous non-polymeric materials or oligomers or mixtures thereof that are insoluble under the low temperature limit workup conditions and contain fluorous domains.

Some specific examples include but are not limited to $CF_3(CF_2)_{10}CF_3$ (mp 76° C.), $CF_3(CF_2)_{12}CF_3$ (mp 103° C.), $CF_3(CF_2)_{14}CF_3$ (125° C.), $CF_3(CF_2)_{18}CF_3$ (mp 162-169° C.), $CF_3(CF_2)_8CF_2H$ (mp 32° C.), $(F_3C)_3CC(CF_3)_3$ (mp 39° C.).

As used herein, the term "solid adsorbent containing a fluorous domain" refers, generally, to solid compounds such as those described above, onto which a fluorous domain has been incorporated. As used herein, the term "biomaterial" refers, generally, to a biopolymer or solid of biological origin, known to those having skill in the art. Examples of biomaterials include, but are not limited to, nucleic acids, peptides, polysaccharides, micelles, lipids, diatomaceous earth, oligomers of peptides, nucleic acids and saccharides, and combinations thereof.

Examples of the form of the adsorbants listed in (1)-(8) above include but are not limited to pellets, powders, amorphous solids, gels, or a coating on yet another material. These phases can be readily separated from fluid phases by standard techniques such as decantation, filtration or centrifugation, among others.

The present invention relates to stoichiometric and catalytic chemical transformations carried out using fluorous catalysts and reagents, which have the general property of fluorous temperature dependent solubilities (FTDS). The FTDS system consists of a reagent or a catalyst containing a sufficient number of fluorous moieties to impart temperature-dependent solubility. The solvent may be any known organic or nonorganic solvent(s). The reaction can occur in solution or at the interface of the solution and any non-dissolved fluorous species. It is important that the attached fluorous moieties do no impair the ability of the catalyst or reagent to be effective or participate in the reaction. The most appropriate fluorous moieties are linear, branched and carbocyclic fluorocarbon alkyl chains with high carbon numbers. The fluorous moieties, optionally, may also contain O, S, N, P, As and Si. The FTDS reagents and ligands can be prepared by: (1) fluorination (i.e., replacement of C—H bonds with fluorine); (2) fluorofunctionalization, e.g., the attachment of fluorous moieties to the reagents or catalysts; or (3) by total synthesis. Many of the catalysts and reagents in the present invention are derivatives of known compounds. Thus they may be used in the reactions and for the purposes known in the art, with the added benefit that their reactive separation from non-fluorous compounds may be facilitated due to their highly temperature dependent solubilities.

Embodiments of the present invention include a solid or liquid fluorous compound (i.e., a reagent or catalyst) and a (non-fluorous) liquid phase in which the fluorous compound has temperature dependent solubility. Also included are the products produced by the processes disclosed herein. The present invention is advantageous because it eliminates the need for liquid-liquid biphase systems, or the tedious mechanical separation of a very small amount of fluorous solid (since the adsorbant provides increased mass). There is no waste water or waste solvent or expensive ionic liquid or fluorous solvent requirement.

As used herein the terms "fluorinated hydrocarbon" and "fluorohydrocarbon" include organic compounds in which at least one hydrogen atom bonded to a carbon atom is not replaced with a fluorine atom. The terms "fluorocarbon" and "perfluorocarbon" mean an organic compound in which all hydrogen atoms bonded to carbon atoms are replaced with fluorine atoms. As used herein, the term "fluorous", when used in connection with an organic (carbon-containing) molecule, moiety or group, refers, generally, to an organic molecule, moiety or group having a domain or a portion thereof rich in carbon-fluorine bonds (for example, fluorocarbons or perfluorocarbons, fluorohydrocarbons, fluorinated ethers, fluorinated amines and fluorinated adamantyl groups). For example, perfluorinated ether groups can have the general formula —[$(CF_2)_xO(CF_2)_y$]$_z CF_3$, wherein x, y and z are integers. Perfluorinated amine groups can, for example, have the general formula —[$(CF_2)_x(NR^a)(CF_2)_y$]$_z CF_3$, wherein $R^a$ can, for example, be $(CF_2)_n CF_3$, wherein n is an integer. Fluorous ether groups and fluorous amine groups suitable for use in the present invention need not be perfluorinated, however. Typically this means that the "fluorous" organic molecule must contain a significant number of hydrogen atoms in C—H bonds replaced with fluorine atoms. Replacement with at least about 20 wt % fluorine to less than about 90 wt % of the total composition is desirable for FTDS reagents and FTDS catalysts. Typically replacement of at least 50 wt % fluorine to total composition of the solvent molecules is desirable. A few examples of suitable fluorous groups, Rf, for use in the present invention include, but are not limited to, —$C_4F_9$, —$C_6F_{13}$, —$C_8F_{17}$, —$C_{10}F_{21}$, —$C(CF_3)_2C_3F_7$, —$C_4F_8CF(CF_3)_2$, —$CF_2CF_2OCF_2CF_2OCF_3$, —$CF_2CF_2(NCF_2CF_3)CF_2CF_2CF_3$, fluorous adamantyl groups, and/or mixtures thereof.

Perfluoroalkyl groups and hydrofluoroalkyl groups are well suited for use in the present invention. For example, Rf can be a linear perfluoroalkyl group of 3 to 20 carbons, a branched perfluoroalkyl group of 3 to 20 carbons, and a hydrofluoroalkyl group of 3 to 20 carbons. Hydrofluoroalkyl groups may typically include up to one hydrogen atom for each two fluorine atoms. In the case of perfluoroalkyl groups and hydrofluoroalkyl groups, Rf may be a linear perfluoroalkyl group of 6 to 12 carbons, a branched perfluoroalkyl group of 6 to 12 carbons, and a hydrofluoroalkyl group of 6 to 12 carbons.

Herein the catalyst is referred to as "fluorous catalyst" and when it exhibits significant temperature dependant solubilities it may be an "FTDS catalyst" and the reagent is referred to as a "fluorous reagent" and when it exhibits significant temperature dependant solubilities it may be an "FTDS reagent". As used herein "reagent" means a compound that is used in a stoichiometric chemical transformation during which it becomes spent but wherein the spent reagent may be regenerated. While reagents and catalysts are used to exemplify the invention, those skilled in the art will recognize that it is applicable to substantially any component of a chemical reaction, including but not limited to substrates, starting materials, reactants, scavengers, side products, byproducts or target products. The present invention includes chemical transformations wherein fluorous compounds are transformed into fluorous products and also includes chemical transformations wherein chemical reactants, such as non-fluorous reactants, are transformed into chemical products, such as non-fluorous products. The present invention substantially allows the easy separation of reaction components that bear fluorous domains (sometimes called tags, labels or pony tails) from those that do not. The fluorous catalysts and reagents should be designed to contain effective amounts and types of fluorous moieties, $(R)_n(Rf)_m$, to confer highly temperature dependent solubility without affecting their activity and reactivity, respectively. Such fluorous moieties are suitably fluorohydrocarbon chains and/or fluorocarbon chains of appropriate length, number and structure to achieve the foregoing purposes.

The present invention teaches a significant advance in reaction processes and reactive separation technology. The present invention allows tailoring of a known catalyst or reagent to confer a high temperature dependent solubility in any solvent while maintaining its ability to carry out or participate in reactions of the corresponding non-fluorous catalyst or reagent (i.e. the catalyst or reagent without the fluorous moiety). An advantage of the present invention is that it permits the carrying out of known catalytic and stoichiometric reactions, the improvement being that incorporation of fluorous moieties in effective amounts render the catalyst or reagent temperature-dependent soluble and allow the reactions to be carried out in a manner that facilitates separation of the fluorous catalyst or spent fluorous reagent from the reaction products (as summarized above), and essentially allows catalyst recycling and reagent regeneration. Also, fluorous systems have remarkable stability even in strongly oxidizing environments.

The process and compositions of the present invention have utility in that they enable known stoichiometric and catalytic reactions to be carried out in a homogeneous environment at an elevated temperature. The catalyst or spent reagent precipitates at a lower temperature, assisted by physical interactions with the adsorbant, thereby facilitating reactive separation of the fluorous catalyst or spent fluorous reagent from other compounds.

In general, an advantage of the present invention is the catalytic and stoichiometric reactions and separations related to the fluorous catalysts and reagents may be carried out within the range of reaction and system conditions and parameters e.g. temperature, pressure, and the like, typically used for the corresponding non-fluorous (parent) catalyst or reagent.

The present invention takes advantage of the previously-established limited solubility or complete insolubility of partially and fully fluorinated hydrocarbon compounds in organic and non-organic solvents or liquid phases, and their significantly higher solubilities at higher temperatures. The fluorous systems used in the present invention consist of: (1) one or more non-fluorous liquid phases containing the reactants; (2) a reagent (i.e. fluorous reagent) or catalyst (i.e. fluorous catalyst) which contains a sufficient number of fluorous moieties having the formula, $(R)_n(Rf)_m$, wherein $(R)_n$, if present, is a hydrocarbon or substituted hydrocarbon domain and/or a heteroatomic or metallic spacer (for example, P, O, N, S, As, Si, Ge, B, Cl, Sn, Pb with appropriate substituents), and wherein $(Rf)_m$ is at least one fluorous domain to confer high temperature-dependent solubility with regard to the liquid in (1). It is acceptable that the reaction educts and/or product(s) alone constitute the liquid phase. The invention is designed such that part or even all of the reagent or catalyst may be dissolved or released into the liquid phase during the chemical reaction such as, for example, by heating or by adding a cosolvent or other additive to help dissolve or release the fluorous catalyst or reagent. As used herein, the term "additive" refers, generally, to any solid or liquid solute or an organic or inorganic nature that may be added to the chemical reaction. For the separation, conditions are selected to drive the fluorous reaction component out of the liquid phase and onto the adsorbant. For example, the reaction mixture may be cooled or a solvent may be added or removed. However, when the solubility of the reagent or catalyst is very low in the liquid phase, there is potential for reaction at the interface. In heterogeneous systems, it can often be difficult to determine in what phase(s) the reaction occurs. This determination is of no concern for the present invention.

The FTDS reagent or FTDS catalyst must be such that it exhibits very low (less than 0.01 M) or complete insolubility at a lower temperature, but much higher solubility at higher temperatures. The FTDS reagent or catalyst may be selected from the group consisting of fluorocarbon and fluorohydrocarbon rich molecules, either of the foregoing with or without functional groups. The presence of structural features that create attractive interactions between the functional groups could limit the solubility and should be minimized. Furthermore, the presence of structural features that allow attractive interactions with the constituents of the liquid phase could lead to leaching. Such leaching is not generally desirable. The most appropriate $(Rf)_m$ groups in this regard are linear, zigzagged (i.e. oxygen and sulfur-containing), carbocyclic, or branched. However, branched groups may be more appropriate (i.e. branching through C or N frameworks) fluorocarbon chains. In some embodiments, higher carbon number chains may be used (e.g., about $C_3$ to about $C_{25}$, more preferably about $C_3$ to about $C_{15}$). The fluorocarbon chain may also include other functional groups, (e.g., aromatic rings).

Such FTDS systems have particular, but not exclusive, applicability in reactions involving known reagents and known catalytic reactions. One of the most important advantages of FTDS systems is the ease of separation of the fluorous catalysts or the spent fluorous reagents from the reaction products, using the adsorbant described above.

FTDS reagents and FTDS catalysts may be obtained by a number of methods. Some reagents and ligands for catalysts may be purchased commercially. Examples of such reagents are: perfluorooctyl-(p-fluorobenzene)iodonium trifluoromethanesulfonate, perfluorodecanoic acid, perfluoro-2,5-dimethyl-3,6-dioxanonanoic acid, perfluorooctane sulfonic acid (K salt), bis(heptafluoro-isopropyl)ketone. Examples of such ligands are: hexafluoroacetylacetone, heptafluorobutyronitrile 1H, 1H,9H-hexadecafluoro-1-nonanol, decafluoro-2-methyl-3-oxahexanoic acid, 1H, 1H-heptafluoro-1-butanol, 11H-eicosafluoroundecanoic acid, 1H, 1H, 11H-eicosafluoro-undecanol-1, heptafluorobutyric acid. Others may be synthesized, by one or more of the following three methods: (1) fluorination of a starting reagent or catalyst, i.e. by full or partial replacement of hydrogen atoms bonded to carbon atoms of the parent catalyst or reagent with fluorine atoms to form the fluorous derivative; (2) fluorofunctionalization of a starting reagent or catalyst, i.e. by incorporation of fluorous moieties, $(Rf)_m$, which may contain, if necessary, appropriate hydrocarbon domain, $(R)_n$, therein; or (3) total synthesis, i.e. de novo synthesis from appropriate building blocks.

When the structural requirements of the FTDS catalyst or reagent allow the complete replacement of all hydrogens bonded to carbons, fluorination can be performed by either using $F_2$/inert gas mixture or other fluorinating agents, (e.g., $CoF_3$). Highly HF-soluble compounds can be perfluorinated by known electrochemical methods. Thermally stable aromatic C—H bond containing reagents and catalysts can be perfluoroalkylated using perfluoroalkyliodides at high temperatures, e.g. 200-300° C. These reactions result in the replacement of hydrogen atoms in the aromatic C—H bonds with perfluoroalkyl chains. The addition of a perfluoroalkyl iodide to olefin flnctionalities on catalysts and reagents also can be used. In both cases thermal or photochemical activation can be applied. For the introduction of fluorous moieties (i.e. $(R)_n(Rf)_m$)) standard C—C coupling reactions could be used. In each instance, the result is a FTDS reagent or FTDS catalyst that is similar to the "parent" (non-fluorous) compound but contains at least one fluorous moiety of suitable length and structure to give the catalyst or reagent highly temperature dependent solubility.

Also included in this invention are processes that use gaseous reactants. These may require high-speed stirring, agitation, or other means of facilitating transport into the liquid reaction medium.

The temperature-dependent solubility of the FTDS catalyst or FTDS reagent with respect to organic and non-organic solvents, coupled with an adsorbant containing fluorous domains, are essential elements for the separation processes disclosed herein. Ideally, the $(R)_n(Rf)_m$ moieties should be introduced such that high solubility at higher temperatures is obtained, with no solubility at a lower temperature. However, there may nonetheless be a measurable degree of solubility at the lower temperature limit. Typically, solubility of the fluorous catalyst or reagent at the 0.01 M level is acceptable.

Chemical transformations can be effected by FTDS catalysts or reagents that contain at least one metal center or organic core. That is, catalysts and reagents known to those skilled in the art to effect or participate in known reactions are potential "parent" materials for making the fluorous phase compatible derivatives of the present invention. However, whether derived from a known parent compound or synthesized de novo, fluorous catalysts and reagents of the present invention that contain at least one metal center, structurally may be represented according to the formula as below: $M_x\{L[(R)_n(Rf)_m]_y\}_z$.

In the above formula the FTDS reagent or FTDS catalyst contains at least one metal center to which at least one fluorous ligand having the formula, $L[(R)_n(Rf)_m]_y$ is bonded which ligand contains the fluorous moiety, i.e. $[(R)_n(Rf)_m]$, which includes the hydrocarbon domain, $(R)_n$, and the fluorous domain, $(Rf)_m$.

For organic-based FTDS catalysts and reagents the formula is: $D[(R)_n(Rf)_m]_y$ wherein D is an organic core to which at least one fluorous moiety is bonded, i.e. $[(R)_n(Rf)_m]$, which may include the hydrocarbon domain, $(R)_n$, and the fluorous domain, $(Rf)_m$.

In both the above formulas, $(Rf)_m$ is a fluorous domain, $(R)_n$ is a hydrocarbon domain that may contain H and C, or may contain groups containing O, N, S, P, As and Si in addition to H and C in the backbone and/or as substituents, but wherein $(R)_n$ is hydrogen atom rich in comparison to $(Rf)_m$, and wherein n is an integer equal to at least zero or any whole number, preferably 0, 1, 2; and wherein m is any whole number; and wherein L is a ligand core containing C, N, O, P, As, S, Si and, in combination with the foregoing, H; and wherein y is the maximum number of fluorous moieties attachable to L or to D, as the case may be; and wherein z is the maximum number of ligands attachable to the metal M. Changing the ratio between n and m, could have major impact on the reactivity of a fluorous catalyst or reagent because fluorous domains are strongly electron withdrawing. Addition of hydrocarbon domains (at least about 2, preferably at least 3 "—$CH_2$—" groups, for example) as spacer groups between L or D and the fluorous domain generally reduces the electron withdrawing effect of the fluorous domain on M or D of the FTDS catalyst or FTDS reagent. The catalysts and reagents typically may contain a plurality of such fluorous moieties (i.e. y is greater than 1) having a significant proportion of fluorine atoms. By significant proportion is meant at least about 20 wt %, typically about 20 to 90 wt %, and in some embodiments from about 50 to 90 wt % of fluorine to total weight of the composition. Variability within $(R)_n$, $(Rf)_m$ and M or D may be introduced to accommodate catalysts or reagents having, for example, multiple metal centers, or variation in the types of ligands. Thus when the particular subscript n, m, y, or z is greater than 1 each n, m, y and z may be the same or different. In all such cases the foregoing should be present in number and structure that are effective to impart high temperature-dependent solubility to the FTDS catalyst or FTDS reagent. Incorporation of O, N, P, As, S, or Si into the carbon backbone of at least one fluorous domain, $(Rf)_m$, may assist in fine-tuning the solubility properties.

The fluorous domain, $(Rf)_m$, typically will have a rod-like structure especially when derived from longer straight chain carbon containing backbones. In addition to L, the FTDS catalyst may contain other ligands. Typically, other ligands known in the art to be used in homogeneous catalysis for a particular reaction may be incorporated into the catalyst when the FTDS catalyst is a modification or derivative of a known parent catalyst. Variability within $(R)_n$, $(Rf)_m$ and M or D may be introduced to accommodate systems having, for example, multiple metal centers, or variation in the types of ligands. Such systems are well known homogeneous catalysts or reagents and are amendable to fluorofunctionalization ("ponytailing") as described herein.

Thus, for example, for the novel catalyst Cl—Rh—{P[CH$_2$—CH$_2$ (CF$_2$)$_6$F]$_3$}$_3$ (the non-fluorous parent compound of which is known as Wilkinson's catalyst, and is used for hydrogenation reactions), Rh corresponds to the Mx wherein M=Rh, x=1; P corresponds to L; —CH$_2$—CH$_2$— corresponds to (R), n=1; —(CF$_2$)$_6$—F to (Rf), m=1; the subscript 3 to y and the final subscript 3 to z. Similarly, for the FTDS reagent, CH$_2$=P[CH$_2$—CH$_2$(CF$_2$)$_7$CF$_3$]$_3$, (the non-fluorous parent compound of which is known as the Wittig reagent), D in the above formula is CH$_2$=P; —CH$_2$CH$_2$— is (R); n=1; —(CF$_2$)$_6$—F is (Rf); m=1; and y is 3. Another FTDS reagent of the same formula would be HOOC—[CH$_2$—CH$_2$(CF$_2$)$_7$CF$_3$]. Thus HOOC— group would correspond to D in the formula.

For adsorbants of the types (5) through (8), fluorous domains are defined as $(Rf)_m$ as defined in the above paragraphs.

By way of example of the utility of such processes are the following examples. Any number of other known processes, e.g. hydrogenation of unsaturated molecules, hydroformylation, polymerization of olefins, asymmetric hydrogenation, epoxidation, hydroformylation, carbon-carbon coupling, suitable may be practiced in accordance with the teaching of the present invention.

The hydroformylation of olefins is an important industrial process for the production of aldehydes from olefins, carbon monoxide, and hydrogen in the presence of homogeneous cobalt or rhodium catalysts. One of the most challenging problems associated with commercial processes is the separation of high molecular weight aldehydes from the catalysts. The use of an aqueous/organic liquid/liquid biphase system, in which the water phase contains the dissolved transition metal catalysts, offers the easy separation of the organic products. However, because the catalytic reaction occurs in the aqueous phase, the potential application of the aqueous biphase system is limited by the solubility of the olefin in the water phase. In contrast, it is expected that FTDS systems may be used for a variety of olefins, as the normal reaction solvents can be used.

The present invention will be described further by reference to the following examples. The following examples are merely illustrative of the invention and are not intended to be limiting. Unless otherwise indicated, all parts are by weight.

EXAMPLES

1) Teflon® Shavings

Phosphine-Catalyzed Hydroalkoxylation of methyl propiolate: Recycling Experiments. A 4 mL screw-top vial was charged with Teflon® shavings (about two layers on the bottom of the vial, average x/y/z dimension ca. 2 mm), P((CH$_2$)$_2$(CF$_2$)$_7$CF$_3$)$_3$ (0.0686 g, 0.050 mmol), n-undecane GC standard (0.3-0.5 mmol added gravimetrically), benzylic alcohol (1.00 mmol), methyl propiolate (0.0421 g, 0.500 mmol) and n-octane (0.80 mL). The sample was stirred at 65° C. for 8 h, and stored at −30° C. overnight. The light yellow organic phase was carefully removed from the supported catalyst via syringe. The residue was shaken with cold n-octane (0.8 mL, −30° C.), and the octane layer similarly separated. The organic phases were combined. An aliquot (0.200 mL) was filtered through a silica gel plug (1 cm) with ethyl acetate/hexanes (10 mL, 1:10 v/v). The filtrate was analyzed by GC (0.0010 mL autoinjection). The vial with the supported catalyst was again charged with n-undecane, benzylic alcohol, methyl propiolate, and octane, and the procedure repeated (yields of E-C$_6$H$_5$CH$_2$OCH=CHCO$_2$CH$_3$ for six cycles: 82%, 82%, 81%, 83%, 81%, 82%)

Catalyst Recovery. A 4 mL screw-top vial was charged with a stir bar, P((CH$_2$)$_2$(CF$_2$)$_7$CF$_3$)$_3$ (0.0653 g, 0.0476 mmol), benzylic alcohol (0.1081 g, 1.000 mmol), methyl propiolate (0.0421 g, 0.500 mmol) and n-octane (0.8 mL). The sample was stirred at 65° C. for 8 h, and Teflong shavings (average x/y/z dimension ca. 2 mm) were added. The sample was kept at −30° C. overnight. The light yellow liquid phase was carefully removed from the catalyst/Teflon® residue by a syringe fitted with a filter. The residue was shaken with cold n-octane (0.8 mL, −30° C.). The suspension was allowed to settle (5 min), and the liquid phase similarly removed. The liquid phases were combined and a standard solution of PPh$_3$ in CF$_3$C$_6$H$_5$ was added (0.0797 M, measured gravimetrically: 0.002182 g, 0.008472 mmol). The solid residue was treated with a solution of PPh$_3$ in CF$_3$C$_6$H$_5$ (0.111 M, 2.0 mL, measured gravimetrically: 0.0581 g, 0.222 mmol). Both samples were analyzed by $^{31}$P inverse-gated NMR (organic phase: 0.2% phosphine oxide leaching, catalyst residue: 98.7% phosphorus recovery).

Identical experiments were conducted in which solutions of C$_6$F$_6$ in CF$_3$C$_6$H$_5$ (for catalyst residue: 0.112 M, 2.0 mL, measured gravimetrically: 0.0424 g, 0.223 mmol; for octane solution: 0.0618 M, 5.0 mL, measured gravimetrically: 0.001304 g, 0.007010 mmol) were used in place of PPh$_3$. Both samples were analyzed by $^{19}$F NMR (organic phase: 1.1%, fluorine leaching, catalyst phase: 98.0% fluorine recovery).

2) No Support

Phosphine-Catalyzed Hydroalkoxylation f Methyl Propiolate: Recycling Experiments. A 4 mL screw-top vial was charged with P((CH$_2$)$_2$(CF$_2$)$_7$CF$_3$)$_3$ (0.0686 g, 0.050 mmol), n-undecane GC standard (0.3-0.5 mmol added gravimetrically), a benzylic alcohol (1.00 mmol), methyl propiolate (0.0421 g, 0.500 mmol) and n-octane (0.80 mL). The sample was stirred at 65° C. for 8 h, and stored at −30° C. overnight. The light yellow organic phase was carefully removed from the solid or gum-like catalyst via syringe. The residue was shaken with cold n-octane (0.8 mL, −30° C.), and the octane layer similarly separated. The organic phases were combined. An aliquot (0.200 mL) was filtered through a silica gel plug (1 cm) with ethyl acetate/hexanes (10 mL, 1:10 v/v). The filtrate was analyzed by GC (0.0010 mL autoinjection). The vial with the catalyst was again charged with n-undecane, benzylic alcohol, methyl propiolate, and octane, and the procedure repeated (yields of E-$C_6H_5CH_2OCH=CHCO_2CH_3$ for six cycles: 82%, 82%, 80%, 81%, 75%, 56%).

Catalyst Recovery. A 4 mL screw-top vial was charged with a stir bar, $P((CH_2)_2(CF_2)_7CF_3)_3$ (0.0653 g, 0.0476 mmol), benzylic alcohol (0.1081 g, 1.000 mmol), methyl propiolate (0.0421 g, 0.500 mmol) and n-octane (0.8 mL). The sample was stirred at 65° C. for 8 h, and kept at −30° C. overnight. The light yellow liquid phase was carefully removed from the catalyst residue by a syringe fitted with a filter. The residue was shaken with cold n-octane (0.8 mL, −30° C.). The suspension was allowed to settle (5 min), and the liquid phase similarly removed. The liquid phases were combined and a standard solution of $PPh_3$ in $CF_3C_6H_5$ was added (0.0797 M, measured gravimetrically: 0.002182 g, 0.008472 mmol). The solid residue was treated with a solution of $PPh_3$ in $CF_3C_6H_5$ (0.111 M, 2.0 mL, measured gravimetrically: 0.0581 g, 0.222 mmol). Both samples were analyzed by $^{31}P$ inverse-gated NMR (organic phase: 6.4% phosphorus leaching, catalyst residue: 91.7% phosphorus recovery).

Identical experiments were conducted in which solutions of $C_6F_6$ in $CF_3C_6H_5$ (for catalyst residue: 0.112 M, 2.0 mL, measured gravimetrically: 0.0424 g, 0.223 mmol; for octane solution: 0.0618 M, 5.0 mL, measured gravimetrically: 0.001304 g, 0.007010 mmol) were used in place of $PPh_3$. Both samples were analyzed by $^{19}F$ NMR (organic phase: 7.4%, fluorine leaching, catalyst phase: 92.3% fluorine recovery).

3) Fluorous Reverse Phased (FRP) Silica

Phosphine-Catalyzed Hydroalkoxylation of Methyl Propiolate: Recycling Experiments. A 4 mL screw-top vial was charged with fluorous reverse phased silica gel (1.0 g), $P((CH_2)_2(CF_2)_7CF_3)_3$ (0.0686 g, 0.050 mmol), n-undecane GC standard (0.3-0.5 mmol added gravimetrically), benzylic alcohol (1.00 mmol), methyl propiolate (0.0421 g, 0.500 mmol) and n-octane (0.80 mL). The sample was stirred at 65° C. for 8 h, and stored at −30° C. overnight. The light yellow organic phase was carefully removed from the supported catalyst via syringe. The residue was shaken with cold n-octane (0.8 mL, −30° C.), and the octane layer similarly separated. The organic phases were combined. An aliquot (0.200 mL) was filtered through a silica gel plug (1 cm) with ethyl acetate/hexanes (10 mL, 1:10 v/v). The filtrate was analyzed by GC (0.0010 mL autoinjection). The vial with the supported catalyst was again charged with n-undecane, benzylic alcohol, methyl propiolate, and octane, and the procedure repeated (yields of E-$C_6H_5CH_2OCH=CHCO_2CH_3$ for six cycles: 80%, 81%, 83%, 80%, 82%, 81%).

Catalyst Recovery. A 4 mL screw-top vial was charged with a stir bar, $P((CH_2)_2(CF_2)_7CF_3)_3$ (0.0653 g, 0.0476 mmol), benzylic alcohol (0.1081 g, 1.000 mmol), methyl propiolate (0.0421 g, 0.500 mmol) and n-octane (0.8 mL). The sample was stirred at 65° C. for 8 h, and fluorous reverse phased silica gel (1.0 g) as a catalyst support was added. The sample was kept at −30° C. overnight. The light yellow liquid phase was carefully removed from the catalyst/silica residue by a syringe fitted with a filter. The residue was shaken with cold n-octane (0.8 mL, −30° C.). The suspension was allowed to settle (5 min), and the liquid phase similarly removed. The liquid phases were combined and a standard solution of $PPh_3$ in $CF_3C_6H_5$ was added (0.0797 M, measured gravimetrically: 0.002182 g, 0.008472 mmol). The solid residue was treated with a solution of $PPh_3$ in $CF_3C_6H_5$ (0.111 M, 2.0 mL, measured gravimetrically: 0.0581 g, 0.222 mmol). Both samples were analyzed by $^{31}P$ inverse-gated NMR (organic phase: 0.1% phosphine oxide leaching, catalyst residue: 98.9% phosphorus recovery).

Identical experiments were conducted in which solutions of $C_6F_6$ in $CF_3C_6H_5$ (for catalyst residue: 0.112 M, 2.0 mL, measured gravimetrically: 0.0424 g, 0.223 mmol; for octane solution: 0.0618 M, 5.0 mL, measured gravimetrically: 0.001304 g, 0.007010 mmol) were used in place of $PPh_3$. Both samples were analyzed by $^{19}F$ NMR (organic phase: 1.0%, fluorine, catalyst phase: 98.3% fluorine recovery).

4) Fluorous Polymer

Phosphine-Catalyzed Hydroalkoxylation of E-benzyloxymethylacrylate: Recycling Experiments. A 4 mL screw-top vial was charged with the fluorous polymer (—CH$(CO_2CH_2CH_2N(C_2H_5)SO_2(CF_2)_7CF_3)CH_2$—)$_n$ (1.0 g) as a catalyst support (see Bergbreiter, D. E.; Franchina, J. G.; *J. Chem. Soc., Chem. Commun.* 1997, 1531), $P((CH_2)_2(CF_2)_7CF_3)_3$ (0.0686 g, 0.050 mmol), n-undecane GC standard (0.3-0.5 mmol added gravimetrically), benzylic alcohol (1.00 mmol), methyl propiolate (0.0421 g, 0.500 mmol) and n-octane (0.80 mL). The sample was stirred at 65° C. for 8 h, and stored at −30° C. overnight. The light yellow organic phase was carefully removed from the supported catalyst via syringe. The residue was shaken with cold n-octane (0.8 mL, −30° C.), and the octane layer similarly separated. The organic phases were combined. An aliquot (0.200 mL) was filtered through a silica gel plug (1 cm) with ethyl acetate/hexanes (10 mL, 1:10 v/v). The filtrate was analyzed by GC (0.0010 mL autoinjection). The vial with the supported catalyst was again charged with n-undecane, benzylic alcohol, methyl propiolate, and octane, and the procedure repeated (yields of E-$C_6H_5CH_2OCH=CHCO_2CH_3$ for six cycles: 80%, 82%, 81%, 82%, 83%, 81%).

Catalyst Recovery. A 4 mL screw-top vial was charged with a stir bar, $P((CH_2)_2(CF_2)_7CF_3)_3$ (0.0653 g, 0.0476 mmol), benzylic alcohol (0.1081 g, 1.000 mmol), methyl propiolate (0.0421 g, 0.500 mmol) and n-octane (0.8 mL). The sample was stirred at 65° C. for 8 h, and the fluorous polymer (—CH$(CO_2CH_2CH_2N(C_2H_5)SO_2(CF_2)_7CF_3)CH_2$—)$_n$ (1.0 g) as a catalyst (see Bergbreiter, D. E.; Franchina, J. G.; *J. Chem. Soc., Chem. Commun.* 1997, 1531) support was added. The sample was kept at −30° C. overnight. The light yellow liquid phase was carefully removed from the catalyst/polymer residue by a syringe fitted with a filter. The residue was shaken with cold n-octane (0.8 mL, −30° C.). The suspension was allowed to settle (5 min), and the liquid phase similarly removed. The liquid phases were combined and a standard solution of $PPh_3$ in $CF_3C_6H_5$ was added (0.0797 M, measured gravimetrically: 0.002182 g, 0.008472 mmol). The solid residue was treated with a solution of $PPh_3$ in $CF_3C_6H_5$ (0.111 M, 2.0 mL, measured gravimetrically: 0.0581 g, 0.222 mmol). Both samples were analyzed by $^{31}P$ inverse-gated NMR (organic phase: 0.1% phosphine oxide leaching, catalyst residue: 99.2% phosphorus recovery).

Identical experiments were conducted in which solutions of $C_6F_6$ in $CF_3C_6H_5$ (for catalyst residue: 0.112 M, 2.0 mL, measured gravimetrically: 0.0424 g, 0.223 mmol; for octane solution: 0.0618 M, 5.0 mL, measured gravimetrically: 0.001304 g, 0.007010 mmol) were used in place of $PPh_3$. Both samples were analyzed by $^{19}F$ NMR (organic phase: 1.0%, fluorine leaching, catalyst phase: 98.8% fluorine recovery).

5) Molecular Fluorocarbons

Phosphine-Catalyzed Hydroalkoxylation of E-benzyloxymethylacrylate: Recycling Experiments. A 4 mL screw-top vial was charged with perfluorohexadecane as a catalyst support (1.0 g), $P((CH_2)_2(CF_2)_7CF_3)_3$ (0.0686 g, 0.050 mmol), n-undecane GC standard (0.3-0.5 mmol added gravimetrically), benzylic alcohol (1.00 mmol), methyl propiolate (0.0421 g, 0.500 mmol) and n-octane (0.80 mL). The sample was stirred at 65° C. for 8 h, and stored at −30° C. overnight. The light yellow organic phase was carefully removed from the supported catalyst via syringe. The residue was shaken with cold n-octane (0.8 mL, −30° C.), and the octane layer similarly separated. The organic phases were combined. An aliquot (0.200 mL) was filtered through a silica gel plug (1 cm) with ethyl acetate/hexanes (10 mL, 1:10 v/v). The filtrate was analyzed by GC (0.0010 mL autoinjection). The vial with the supported catalyst was again charged with n-undecane, benzylic alcohol, methyl propiolate, and octane, and the procedure repeated (yields of $E-C_6H_5CH_2OCH=CHCO_2CH_3$ for six cycles: 84%, 83%, 84%, 85%, 84%, 83%).

Catalyst Recovery. A 4 mL screw-top vial was charged with a stir bar, $P((CH_2)_2(CF_2)_7CF_3)_3$ (0.0653 g, 0.0476 mmol), benzylic alcohol (0.1081 g, 1.000 mmol), methyl propiolate (0.0421 g, 0.500 mmol) and n-octane (0.8 mL). The sample was stirred at 65° C. for 8 h, and perfluorohexadecane (1.0 g) as a catalyst support was added. The sample was kept at −30° C. overnight. The light yellow liquid phase was carefully removed from the catalyst/perfluorohexadecane residue by a syringe fitted with a filter. The residue was shaken with cold n-octane (0.8 mL, −30° C.). The suspension was allowed to settle (5 min), and the liquid phase similarly removed. The liquid phases were combined and a standard solution of $PPh_3$ in $CF_3C_6H_5$ was added (0.0797 M, measured gravimetrically: 0.002182 g, 0.008472 mmol). The solid residue was treated with a solution of $PPh_3$ in $CF_3C_6H_5$ (0.111 M, 2.0 mL, measured gravimetrically: 0.0581 g, 0.222 mmol). Both samples were analyzed by $^{31}P$ inverse-gated NMR (organic phase: 0.1% phosphine oxide leaching, catalyst residue: 99.1% phosphorus recovery).

Identical experiments were conducted in which solutions of $C_6F_6$ in $CF_3C_6H_5$ (for catalyst residue: 0.112 M, 2.0 mL, measured gravimetrically: 0.0424 g, 0.223 mmol; for octane solution: 0.0618 M, 5.0 mL, measured gravimetrically: 0.001304 g, 0.007010 mmol) were used in place of $PPh_3$. Both samples were analyzed by $^{19}F$ NMR (organic phase: 1.1%, fluorine, catalyst phase: 98.6% fluorine recovery).

All of the above experiments 1)-5) were also performed with the alcohols $C_6H_5CH(CH_3)OH$, $(C_6H_5)_2CHOH$ and 1-octanol and with the more nucleophilic phosphine $P((CH_2)_3(CF_2)_7CF_3)_3$ with similar results.

Example with a Transition Metal Complex:

Rhodium-Catalyzed Hydrosilylation of Cyclohexanone: Recycling Experiments. A 4 mL screw-top vial was charged with fluorous reverse phased silica gel (1.0 g) as a catalyst support, $ClRh[P(CH_2CH_2(CF_2)_5CF_3)_3]_3$ (8.7 mg, 0.26 μmol, 0.2 mol %), dimethylphenylsilane (219 μL, 1.43 mmol), cyclohexanone (135 μL, 1.30 mmol) and hexane (2.0 mL). The sample was stirred at 60° C. for 3 h, and then froze to −30° C. for 4 h. The top hexane was extracted via syringe. The catalyst/silica residue was shaken with cold hexane (1.0 mL, −30° C.), and the hexane layer similarly separated. The product was distilled from the combined organic phases by Kugelrohr to give a clear fluid (0.274 g, 90%). The vial with the supported catalyst was again charged with dimethylphenylsilane, cyclohexanone and hexane, and the procedure repeated (yields of $C_6H_{11}OSi(CH_3)_2C_6H_5$ for four cycles: 90%, 90%, 85%, 81%).

Although the foregoing description has necessarily presented a limited number of embodiments of the invention, those of ordinary skill in the relevant art will appreciate that various changes in the components, details, materials, and process parameters of the examples that have been herein described and illustrated in order to explain the nature of the invention may be made by those skilled in the art, and all such modifications will remain within the principle and scope of the invention as expressed herein in the appended claims. It will also be appreciated by those skilled in the art that changes could be made to the embodiments described above without departing from the broad inventive concept thereof. It is understood, therefore, that this invention is not limited to the particular embodiments disclosed, but it is intended to cover modifications that are within the principle and scope of the invention, as defined by the claims.

We claim:

1. A method for conducting a chemical reaction in a non-fluorous medium using at least one chemical reactant and a fluorous compound in the presence of a solid adsorbant containing a fluorous domain, the method comprising:

contacting the fluorous compound and the at least one chemical reactant in the non-fluorous medium and in the presence of the solid adsorbant under conditions that form at least one product; and changing at least one reaction condition such that the solubility of the fluorous compound in the non-fluorous medium decreases and the amount of the fluorous compound absorbed on the fluorous domain of the solid adsorbant increases, wherein the changing at least one reaction condition is selected from the group consisting of adjusting a temperature, adjusting a solvent concentration, adding an additive, and combinations thereof, and wherein the fluorous compound comprises at least one fluorous moiety having a formula $—(R)_n(Rf)_m$, where R is independently, the same or different, a hydrocarbon moiety, Rf is independently, the same or different, a fluorous domain, n is an integer equal to at least 0, and m is an integer greater than 0, and wherein the chemical reaction is conducted in the absence of a fluorous solvent, and wherein the at least one product is a different chemical compound than the at least one chemical reactant and the fluorous compound.

2. The method of claim 1, wherein the fluorous compound is transformed into at least one fluorous product.

3. The method of claim 1, wherein the at least one chemical reactant is transformed into at least one chemical product.

4. The method of claim 1, wherein the fluorous compound is a fluorous reagent or a fluorous catalyst.

5. The method of claim 1, wherein the non-fluorous medium further comprises a solvent selected from the group consisting of an organic solvent, an inorganic solvent and mixtures thereof.

6. The method of claim 1, wherein the solid adsorbant containing the fluorous domain is selected from the group consisting of polytetrafluoroethylene, perfluorinated polymers, highly fluorinated polymers, non-fluorous polymers into which fluorous domains have been incorporated, biomaterials into which fluorous domains have been incorporated, inorganic oxides onto which fluorous domains have been introduced, solid polymeric materials onto which fluorous domains have been introduced, extended domain materials onto which fluorous domains have been introduced, non-polymeric materials containing fluorous domains, oligomeric materials containing fluorous domains, and mixtures thereof.

7. The method of claim 1, wherein the solid adsorbant containing the fluorous domain is in a form selected from the group consisting of pellets, shavings, powders, amorphous solids, gels, a coating, and mixtures thereof.

8. The method of claim 1, wherein adjusting the temperature comprises reducing the temperature, and adjusting the solvent concentration is selected from the group consisting of adding at least one organic solvent, adding at least one inorganic solvent, removing an organic solvent, and removing an inorganic solvent.

9. The method of claim 1, wherein the changing at least one reaction condition comprises reducing the temperature of the chemical reaction from a first temperature to a second temperature such that the solubility of the fluorous compound in the non-fluorous medium decreases and the amount of the fluorous compound absorbed on the fluorous domain of the solid adsorbent increases.

10. The method of claim 1, wherein the solubility of the fluorous compound in the non-fluorous medium after changing the at least one reaction condition is less than 0.01 M.

11. The method of claim 1, the method further comprising separating the solid adsorbent containing the fluorous domain with the absorbed fluorous compound from the at least one chemical product.

12. The method of claim 11, wherein the solid adsorbent containing the fluorous domain with the absorbed fluorous compound is separated from the at least one chemical product using a separation technique selected from the group consisting of decantation, filtration, and centrifugation.

13. The method of claim 11, wherein the fluorous compound is a fluorous catalyst, the method further comprising submitting the solid adsorbent containing the fluorous domain with the absorbed fluorous compound to a second chemical reaction.

14. The method of claim 11, wherein the fluorous compound is a fluorous reagent, the method further comprising regenerating the fluorous reagent and submitting the regenerated fluorous reagent to a second chemical reaction.

15. The method of claim 1, wherein the fluorous compound has a general formula:

$$D[(R)_n(Rf)_m]_y,$$

wherein D has a structure selected from the group consisting of an organic group, P, OH, OR, N, S, As, and Si, R is independently, the same or different, a hydrocarbon moiety, Rf is independently, the same or different, a fluorous moiety, n is an integer equal to at least 0, m is an integer greater than 0, and y is an integer between 1 and the maximum number of bonding attachments of D.

16. The method of claim 15, wherein D is phosphorous, R is —$CH_2$—, n is an integer from 2 to 5, m is equal to 1, and y is equal to 3.

17. The method of claim 15, wherein the fluorous compound has a formula $P((CH_2)_2(CF_2)_7CF_3)_3$.

18. The method of claim 1, wherein the fluorous compound has a general formula:

$$M_x\{L[(R)_n(Rf)_m]_y\}_z,$$

wherein M is a metal selected from the group consisting of a transition metal, a lanthanide metal, thorium and uranium, L is a ligand core having a structure selected from the group consisting of C, N, O, P, As, S and Si, R is independently, the same or different, a hydrocarbon moiety, Rf is independently, the same or different, a fluorous moiety, n is an integer equal to at least 0, m is an integer greater than 0, y is an integer between 1 and the maximum number of bonding attachments of L, z is an integer between 1 and the maximum number of ligands attachable to M, and x is an integer from 1 to 4.

19. The method of claim 18, wherein the fluorous compound has a formula $ClRh[P(CH_2CH_2(CF_2)_5CF_3)_3]_3$.

20. A method for conducting a chemical reaction in a non-fluorous medium using at least one chemical reactant and a fluorous compound in the presence of a solid adsorbant containing a fluorous domain, wherein the fluorous compound is initially absorbed on the fluorous domain of the solid adsorbant, the method comprising:
   changing a first reaction condition from a first state to a second state, such that the solubility of the fluorous compound in the non-fluorous medium increases and the amount of the fluorous compound absorbed on the fluorous domain of the solid adsorbant decreases; and
   contacting the fluorous compound and at the least one chemical reactant in the non-fluorous medium and in the presence of the solid adsorbant under conditions that form at least one product,
   wherein the changing the first reaction condition is selected from the group consisting of increasing temperature, adding a co-solvent, adding an additive, and combinations thereof, and
   wherein the fluorous compound comprises at least one fluorous moiety having a formula —$(R)_n(Rf)_m$, where R is independently, the same or different, a hydrocarbon moiety, Rf is independently, the same or different, a fluorous domain, n is an integer equal to at least 0, and m is an integer greater than 0, and
   wherein the chemical reaction is conducted in the absence of a fluorous solvent, and wherein the at least one product is a different chemical compound than the at least one chemical reactant and the fluorous compound.

21. The method of claim 20, wherein the fluorous compound is transformed into at least one fluorous product.

22. The method of claim 20, wherein the chemical reactant is transformed into at least one chemical product.

23. The method of claim 20, wherein the fluorous compound is a fluorous reagent or a fluorous catalyst.

24. The method of claim 20, wherein the non-fluorous medium further comprises a solvent selected from the group consisting of an organic solvent, an inorganic solvent and mixtures thereof.

25. The method of claim 20, wherein the changing the first reaction condition comprises raising the temperature of the chemical reaction from a first temperature to a second temperature, such that the solubility of the fluorous compound in the non-fluorous medium increases and the amount of the fluorous compound absorbed on the fluorous domain of the solid adsorbant decreases.

26. The method of claim 25, wherein the solubility of the fluorous compound in the non-fluorous medium at the first temperature is less than 0.01 M.

27. The method of claim 20, the method further comprising changing a second reaction condition from the second state to a third state, such that the solubility of the fluorous compound in the non-fluorous medium decreases and the amount of the fluorous compound absorbed on the fluorous domain of the solid adsorbant increases,
   wherein the changing at least one reaction condition is selected from the group consisting of adjusting the temperature, adjusting a solvent concentration, adding an additive, and combinations thereof.

28. The method of claim 27, wherein changing the second reaction condition comprises reducing the temperature of the chemical reaction from the second temperature to a third temperature, such that the solubility of the fluorous compound in the non-fluorous medium decreases and the amount of the fluorous compound absorbed on the fluorous domain of the solid adsorbant increases.

29. The method of claim 28, wherein the solubility of the fluorous compound in the non-fluorous medium at the third temperature is less than 0.01 M.

30. The method of claim 20, wherein the solid adsorbant containing the fluorous domain is selected from the group consisting of polytetrafluoroethylene, perfluorinated polymers, highly fluorinated polymers, non-fluorous polymers into which fluorous domains have been incorporated, biomaterials into which fluorous domains have been incorporated, inorganic oxides onto which fluorous domains have been introduced, solid polymeric materials onto which fluorous domains have been introduced, extended domain materials onto which fluorous domains have been introduced, non-polymeric materials containing fluorous domains, oligomeric materials containing fluorous domains and mixtures thereof.

31. The method of claim 20, wherein the solid adsorbant containing the fluorous domain is in a form selected from the group consisting of pellets, shavings, powders, amorphous solids, gels, a coating, and mixtures thereof.

32. The method of claim 27, the method further comprising separating the solid adsorbant containing the fluorous domain with the absorbed fluorous compound from the at least one chemical product.

33. The method of claim 32, wherein the solid adsorbant containing the fluorous domain with the absorbed fluorous compound is separated from the at least one chemical product using a separation technique selected from the group consisting of decantation, filtration, and centrifugation.

34. The method of claim 32, wherein the fluorous compound is a fluorous catalyst, the method further comprising submitting the solid adsorbant containing the fluorous domain with the absorbed fluorous compound to a second chemical reaction.

35. The method of claim 32, wherein the fluorous compound is a fluorous reagent, the method further comprising regenerating the fluorous reagent and submitting the regenerated fluorous reagent to a second chemical reaction.

36. The method of claim 20, wherein the fluorous compound has a general formula:

$$D[(R)_n(Rf)_m]_y,$$

wherein D has a structure selected from the group consisting of an organic group, P, OH, OR, N, S, As, and Si, R is independently, the same or different, a hydrocarbon moiety, Rf is independently, the same or different, a fluorous moiety, n is an integer equal to at least 0, m is an integer greater than 0, and y is an integer between 1 and the maximum number of bonding attachments of D.

37. The method of claim 36, wherein D is phosphorous, R is $-CH_2-$, n is an integer from 2 to 5, m is equal to 1, and y is equal to 3.

38. The method of claim 36, wherein the fluorous compound has a formula $P((CH_2)_2(CF_2)_7CF_3)_3$.

39. The method of claim 20, wherein the fluorous compound has a general formula:

$$M_x\{L[(R)_n(Rf)_m]_y\}_z,$$

wherein M is a metal selected from the group consisting of a transition metal, a lanthanide metal, thorium and uranium, L is a ligand core having a structure selected from the group consisting of C, N, O, P, As, S and Si, R is independently, the same or different, a hydrocarbon moiety, Rf is independently, the same or different, a fluorous moiety, n is an integer equal to at least 0, m is an integer greater than 0, y is an integer between 1 and the maximum number of bonding attachments of L, z is an integer between 1 and the maximum number of ligands attachable to M, and x is an integer from 1 to 4.

40. The method of claim 39, wherein the fluorous compound has a formula $ClRh[P(CH_2CH_2(CF_2)_5CF_3)_3]_3$.

41. A method for conducting a chemical reaction in a non-fluorous medium using a fluorous compound and at least one chemical reactant, the method comprising:
 contacting the fluorous compound and at least one chemical reactant in the non-fluorous medium under conditions that form at least one product;
 adding solid adsorbant containing a fluorous domain; and
 reducing the temperature of the chemical reaction from a first temperature to a second temperature such that the solubility of the fluorous compound in the non-fluorous medium decreases and the amount of the fluorous compound absorbed on the fluorous domain of the solid adsorbant increases,
 wherein the fluorous compound comprises at least one fluorous moiety having a formula $-(R)_n(Rf)_m$, where R is independently, the same or different, a hydrocarbon moiety, Rf is independently, the same or different, a fluorous domain, n is an integer equal to at least 0, and m is an integer greater than 0, and
 wherein the chemical reaction is conducted in the absence of a fluorous solvent, and wherein the at least one product is a different chemical compound than the at least one chemical reactant and the fluorous compound.

42. The method of claim 41, wherein the fluorous compound is transformed into at least one fluorous product.

43. The method of claim 41, wherein the chemical reactant is transformed into at least one chemical product.

44. The method of claim 41, wherein the fluorous compound is a fluorous reagent.

45. The method of claim 41, wherein the fluorous compound is a fluorous catalyst.

46. The method of claim 41, wherein the non-fluorous medium further comprises a solvent selected from the group consisting of an organic solvent, an inorganic solvent and mixtures thereof.

47. The method of claim 41, wherein the solubility of the fluorous compound in the non-fluorous medium at the second temperature is less than 0.01 M.

48. The method of claim 41, wherein the solid adsorbant containing the fluorous domain is selected from the group consisting of polytetrafluoroethylene, perfluorinated polymers, highly fluorinated polymers, non-fluorous polymers into which fluorous domains have been incorporated, biomaterials into which fluorous domains have been incorporated, inorganic oxides onto which fluorous domains have been introduced, solid polymeric materials onto which fluorous domains have been introduced, extended domain materials onto which fluorous domains have been introduced, non-polymeric materials containing fluorous domains, oligomeric materials containing fluorous domains and mixtures thereof.

49. The method of claim 41, wherein the solid adsorbant containing the fluorous domain is in a form selected from the group consisting of pellets, shavings, powders amorphous solids, gels, a coating, and mixtures thereof.

50. The method of claim 41, the method further comprising separating the solid adsorbant containing the fluorous domain with the absorbed fluorous compound from the at least one chemical product.

51. The method of claim 50, wherein the solid adsorbant containing the fluorous domain with the absorbed fluorous compound is separated from the at least one chemical product using a separation technique selected from the group consisting of decantation, filtration, and centrifugation.

52. The method of claim 50, wherein the fluorous compound is a fluorous catalyst, the method further comprising submitting the solid adsorbant containing the fluorous domain with the absorbed fluorous compound to a second chemical reaction.

53. The method of claim 50, wherein the fluorous compound is a fluorous reagent, the method further comprising regenerating the fluorous reagent and submitting the regenerated fluorous reagent to a second chemical reaction.

54. A method for conducting a chemical reaction using at least one chemical reactant and a fluorous compound in a non-fluorous medium, in the presence of a solid adsorbent containing a fluorous domain, wherein the fluorous compound is initially absorbed on the fluorous domain of the solid adsorbant, the method comprising:

increasing the temperature of the chemical reaction from a first temperature to a second temperature, such that the solubility of the fluorous compound in the non-fluorous medium increases and the amount of the fluorous compound absorbed on the fluorous domain of the solid adsorbant decreases;

contacting the fluorous compound and at least one chemical reactant in the non-fluorous medium under conditions that form at least one product; and decreasing the temperature from the second temperature to a third temperature, such that the solubility of the fluorous compound in the non-fluorous medium decreases and the amount of the fluorous compound absorbed on the fluorous domain of the solid adsorbant increases, wherein the fluorous compound comprises at least one fluorous moiety having a formula a $—(R)_n(Rf)_m$, where R is independently, the same or different, a hydrocarbon moiety, Rf is independently, the same or different, a fluorous domain, n is an integer equal to at least 0, and m is an integer greater than 0, and wherein the chemical reaction is conducted in the absence of a fluorous solvent, and wherein the at least one product is a different chemical compound than the at least one chemical reactant and the fluorous compound.

55. The method of claim 54, wherein the non-fluorous medium is selected from the group consisting of an organic solvent, an inorganic solvent, and mixtures thereof.

56. The method of claim 54, wherein the fluorous compound is transformed into at least one fluorous product.

57. The method of claim 54, wherein the chemical reactant is transformed into at least one chemical product.

58. The method of claim 54, wherein the fluorous compound is a fluorous reagent.

59. The method of claim 54, wherein the fluorous compound is a fluorous catalyst.

60. The method of claim 54, wherein the solubilities of the fluorous compound in the non-fluorous solvent at the first temperature and the third temperature are each less than 0.01 M.

61. The method of claim 54, wherein the solid adsorbant containing the fluorous domain is selected from the group consisting of polytetrafluoroethylene, perfluorinated polymers, highly fluorinated polymers, non-fluorous polymers into which fluorous domains have been incorporated, biomaterials into which fluorous domains have been incorporated, inorganic oxides onto which fluorous domains have been introduced, solid polymeric materials onto which fluorous domains have been introduced, extended domain materials onto which fluorous domains have been introduced, non-polymeric materials containing fluorous domains, oligomeric materials containing fluorous domains and mixtures thereof.

62. The method of claim 54, wherein the solid adsorbant containing the fluorous domain is in a form selected from the group consisting of pellets, shavings, powders, amorphous solids, gels, a coating, and mixtures thereof.

63. The method of claim 54, the method further comprising separating the solid adsorbant containing the fluorous domain with the absorbed fluorous compound from the at least one chemical product.

64. The method of claim 63, wherein the solid adsorbant containing the fluorous domain with the absorbed fluorous compound is separated from the at least one chemical product using a separation technique selected from the group consisting of decantation, filtration, and centrifugation.

65. The method of claim 63, wherein the fluorous compound is a fluorous catalyst, the method further comprising submitting the solid adsorbant containing the fluorous domain with the absorbed fluorous compound to a second chemical reaction.

66. The method of claim 63, wherein the fluorous compound is a fluorous reagent, the method further comprising regenerating the fluorous reagent and submitting the regenerated fluorous reagent to a second chemical reaction.

67. The method of claim 1, wherein the chemical reaction is conducted in the absence of pressurized carbon dioxide.

68. The method of claim 41, wherein the chemical reaction is conducted in the absence of pressurized carbon dioxide.

* * * * *